United States Patent [19]

Eriksson et al.

[11] 4,100,210

[45] Jul. 11, 1978

[54] ALKYLCHLORIDE

[75] Inventors: Jan Bertil Eriksson, Visp, Switzerland; Zaven Armen Dadekian, Upper Saddle River, N.J.

[73] Assignee: Lonza A. G., Basel, Switzerland

[21] Appl. No.: 713,263

[22] Filed: Aug. 10, 1976

[30] Foreign Application Priority Data

Aug. 12, 1975 [CH] Switzerland .................. 10461/75

[51] Int. Cl.² .................................. C07C 19/02
[52] U.S. Cl. .................................. 260/652 R

[58] Field of Search .................................. 260/652 R

[56] References Cited

U.S. PATENT DOCUMENTS 3,432,561  3/1969  Dadekian et al. .............. 260/562 R Primary Examiner—C. Davis
Attorney, Agent, or Firm—Bert J. Lewen

[57] ABSTRACT

A process for the preparation of alkyl chlorides by the reaction of an alkyl alcohol with phosphorous trichloride in two reaction stages is disclosed.

9 Claims, 1 Drawing Figure

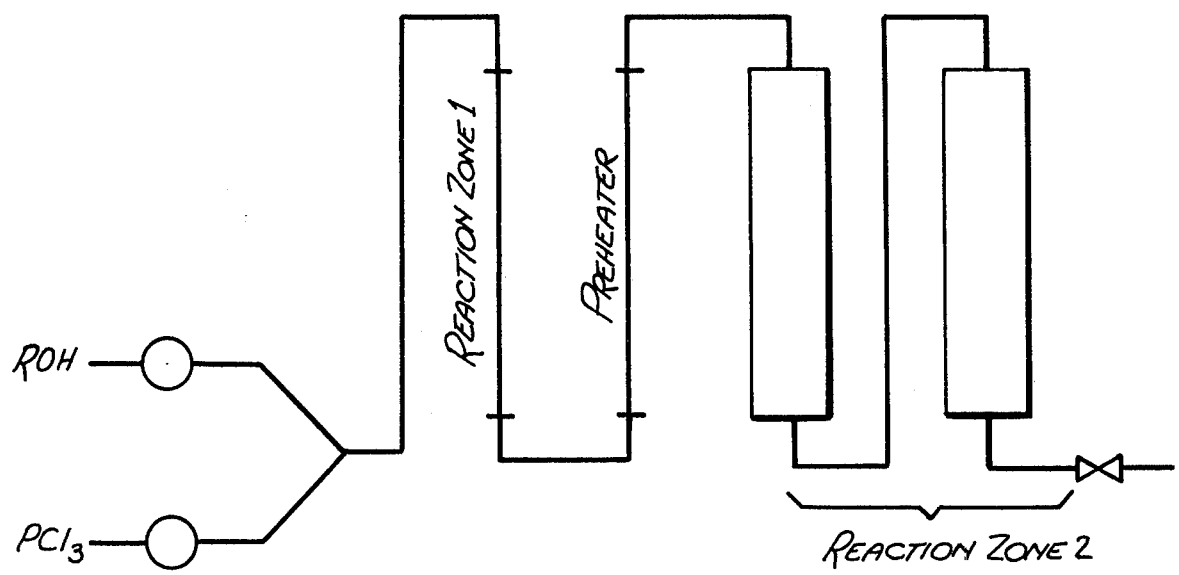

ALKYLCHLORIDE

The invention relates to a process for the preparation of alkyl chlorides by reacting alkyl alcohols with phosphorus trichloride at temperature and elevated pressures.

It is known to prepare alkyl chlorides by reacting alkyl alcohols with phosphorus trichloride (U.S. Pat. No. 3,432,561). In that process, the chlorination is performed batchwise in two stages. In a first stage, the alcohol and the phosphorus trichloride are mixed by maintaining a temperature below 80° C and a pressure of about 6 atm. and the reaction subsequently, in a second stage, the reaction is completed at a temperature of 80° to 150° C and pressures of about 12 atm. Even though it is possible to achieve yields of 98 to 99%, this process, on account of the lengthy reaction period, leaves something to be desired with regard to the spacet-time yield, which is about 0.1 kg alkyl chloride per hour per liter of reactor volume. In this process, particular attention is paid in the first stage so that the temperature does not exceed 80° C., and preferably is maintained at from 50° to 65° C., so as not to form undesirable by-products such as dialkyl ether.

Because of this, the conversion of this process into a continuous process (flow line) with an improved space-time yield did not seem to be possible without large losses in the yield of the desired alkyl chloride.

Surprisingly, it has now however been found that it is possible to increase the space-time yield substantially without any reduction in the yield of alkyl chloride.

According to the invention, this is achieved by using a flow line that is subdivided into three zones: a reaction zone 1, a preheater, and a reaction zone 2, mixing the alcohol and the phosphorus trichloride at a molar ratio from 2.85 : 1 up to 3 : 1 in the reaction zone 1 at temperatures from 85° to 110° C; is subsequently heating the reaction mixture in the preheater to 140°–150° C.; and thereafter completing the reaction in reaction zone 2 at 150°–200° C. with the pressure maintained in said flow line at 25 to 50 atm.

The residence time in reaction zone 1 amounts, preferably, to 2 – 5 minutes, in the preheater, preferably, 2 – 3 minutes, and in the reaction zone 2, preferably, 25 – 35 minutes.

The molar mixing proportion of alcohol to $PCl_3$ is from 2.85 : 1 to 3 : 1, preferably from 2.90 : 1 to 2.95 : 1.

The flow line consists suitably of corrosion-resistant material or is lined with corrosion-resistant material.

In reaction zone 1 there occurs the preliminary reaction. This is exothermic reaction so that this zone is provided with an exterior cooling to maintain the temperatures stationary from 85° to 110° C, preferably 90° to 100° C.

In reaction zone 2 the reaction is completed. In this zone it is necessary to heat preferably to 150° to 180° C, and this zone is therefore provided with external heating. The reaction pressure in the flow line is set and controlled by a relief valve at 25 – 50 atm., preferably 30 atm.

Thereupon there follows a decanter in which the organic phase is separated from the aqueous phase.

By way of alcohols there can be used those having 4 – 22 C atoms, preferably those with 8 – 18 C atoms. Same can be primary, secondary, straight-chain or branched chain. It is possible to use both natural and synthetic alcohols.

Examples of such alcohols are: n-butanol, isobutanol, sec.-butanol, n-amyl alcohol, n-hexanol, n-octanol, capryl alcohol, hendecanol, lauryl alcohol, tridecyl alcohol, myristyl alcohol, pentadecyl alcohol, cetyl alcohol, stearyl alcohol, docosyl alcohol, hexamethylene glycol.

According to the process of the invention, one obtains at yields in excess of 97.5% space-time yields in excess of 1 kg per hour per liter of reactor volume.

EXAMPLE 1

Into a reactor system in accordance with FIG. 1 there were pumped jointly per hour 1.65 kg lauryl alcohol (purity: 97%) and 0.41 kg phosphorus trichloride. The cooling was performed in reaction zone 1 in such a way that the outlet temperature was about 110° C. The residence time in reaction zone 1 was 5 minutes. Following preheating to 150° C for 2.5 minutes, the reaction mixture reached reaction zone 2 in which the reaction temperature was maintained with superheated steam at 165° C. The residence time in reaction zone 2 was 26 minutes. By means of a pressure maintenance valve, the entire reactor system was under a pressure of 30 atm. The product obtained in this manner separated out immediately into two phases. One obtained per hour 1.8 kg of the organic phase corresponding to a yield of 97.5% of lauryl chloride with respect to lauryl alcohol. The purity amounted to 95 weight-percent of lauryl chloride. The product contained 0.14 weight-percent of dilauryl ether. Space-time yield: 1.4 kg/hour, liter.

EXAMPLE 2

Ib a reactor as illustrated in FIG. 1, lauryl alcohol and phosphorus trichloride were pumped in at a molar ratio of 2.90 : 1. The pressure in the flow line was 35 atm. The temperature at the outlet of reaction zone 1 was 90° C and at the outlet of the preheater, 150° C. In reaction zone 2, the temperature was 155° to 160° C. The residence times in reaction zone 1, the preheater, and reaction zone 2 were 2.5, 3.0, and 35 minutes. One obtained an organic phase with 96% lauryl chloride in a yield of 98.9% with respect to the lauryl alcohol. The product contained 0.18% dilauryl ether. Space-time yield: 1.2 kg/hour, liter.

EXAMPLE 3

Into a reactor system in accordance with Example 1 there were pumped octyl alcohol and phosphorus trichloride in a molar ratio of 2.90 : 1. The pressure in the flow line was 30 atm. The residence time in reaction zone 1 was 3 minutes; in the preheater, 2 minutes; and, in reaction zone 2, 28 minutes. The temperature at the outlet of reaction zone 1 was 100° C. Following preheating to 150° C, an average temperature of 150° to 155° C was maintained in reaction zone 2. One obtained in the organic phase 96% octyl chloride in a yield of 98% with respect to octyl alcohol. The product contained 0.19% dioctyl ether. Space-time yield: 1.4 kg/hour, liter.

EXAMPLE 4

Into a reactor system in accordance with Example 1 there were pumped octyl alcohol and phosphorus trichloride in a molar ratio of 2.95 : 1. The pressure in the flow line was 35 atm. The residence time in reaction zone 1 was 2.5 minutes; in the preheater, 2 minutes; and, in reaction zone 2, 24 minutes. The cooling in reaction zone 1 produced an outlet temperature of 90° C. Following preheating to 150° C, an average temperature of 155° to 160° C was maintained in reaction zone 2. One obtained an organic phase containing 95.4% octyl chloride in a yield of 97.5% with respect to octyl alcohol. The product contained 0.14% dioctyl ether. Space-time yield: 1.6 kg/hour, liter.

EXAMPLE 5

In a reactor in accordance with Example 1, cetyl alcohol was reacted with phosphorus trichloride in a molar ratio of 2.95 : 1. Pressure in the flow line was 30 atm. The residence time in reaction zone 1 was 4 minutes; in the preheater, 2 minutes; and, in reaction zone 2, 35 minutes. The temperature at the outlet of reaction zone 1 was 95° C.; In the preheater, 145° C.; and, in the reaction zone 2, an average of 160° C. The yield of cetyl chloride amounted to 96.7% with respect to the cetyl alcohol. The product contained 0.3% dicethyl ether. Space-time yield: 1.1 kg/hour, liter.

EXAMPLE 6

Into a reaction system in accordance with Example 1 there was pumped an alcohol mixture and phosphorus trichloride in a molar ratio of 2.90 : 1. The composition of the alcohol mixture was 6.5% octyl alcohol, 8.1% decyl alcohol, 30.0% dodecyl alcohol, 28% myristyl alcohol, 15.2% cetyl alcohol, and 9% stearyl alcohol. The reaction mixture left reaction zone 1 at a temperature of 90° C, was heated in the preheater to 150° C and subsequently maintained at 155° to 160° C in reaction zone 2. The residence time in reaction zone 1 was 3.5 minutes, in the preheater, 2 minutes; and, in reaction zone 2, 28 minutes. The pressure was 30 atm. One obtained an alkyl chloride mixture corresponding to the alcohol mixture in a yield of 96% with respect to the alcohol charged. Space-time yield: 1.4 kg/hour, liter.

We claim:

1. In a process for the preparation of alkyl chlorides by the reaction of an alkyl alcohol having from 4 to 22 carbon atoms with phosphorus trichloride, the improvement of performing said process in a flow line which is maintained at a pressure of from 25 to 50 atmospheres and divided into a first reaction zone, a preheater, and a second reaction zone, wherein the alcohol and the phosphorus trichloride are fed to the first reaction zone at a temperature of from 85° to 110° C. in a molar ratio of 2.85:1 to 3:1; wherein the reaction mixture from the first reaction zone is passed to the preheater and heated to a temperature of 140° to 150° C.; and wherein the reaction mixture from said preheater is passed to the second reaction zone maintained at a temperature of 150° to 200° C. to substantially complete the reaction.

2. The process of claim 1 wherein the temperature in the first reaction zone is maintained at from 90° to 100° C.

3. The process of claim 1 wherein the temperature in the second reaction zone is maintained at from 150° to 180° C.

4. The process of claim 1 wherein the residence time in the first reaction zone is from 2 to 5 minutes and, in the second reaction zone, from 25 to 35 minutes.

5. The process of claim 1 wherein the alcohol has from 8 to 18 carbon atoms.

6. The process of claim 5 wherein the alcohol is lauryl alcohol.

7. The process of claim 5 wherein the alcohol is octyl alcohol.

8. The process of claim 5 wherein the alcohol is cetyl alcohol.

9. The process of claim 1 wherein the alcohol is a blend of alcohols having differing numbers of carbon atoms.

* * * * *